United States Patent [19]

Tuba et al.

[11] Patent Number: 5,510,345
[45] Date of Patent: Apr. 23, 1996

[54] BIOLOGICALLY ACTIVE EBURNAMENINE DERIVATIVES, PHARMACEUTICAL COMPOSITIONS CONTAINING THEM AND PROCESS FOR PREPARING SAME

[75] Inventors: Zoltán Tuba; Sándor Mahó; Anikó Gere; Pál Vittay; Béla Kiss; Éva Pálosi; László Szporny; Csaba Szántay; Ferenc Sóti; Zsuzsa Baloghné Kardos; Mária Incze; Gábor Balogh; Mária Gazdag, all of Budapest, Hungary

[73] Assignee: Richter Gedeon Vegyeszeti Gyar Rt., Budapest, Hungary

[21] Appl. No.: 351,447

[22] PCT Filed: Jun. 8, 1993

[86] PCT No.: PCT/Hu93/00036

§ 371 Date: Dec. 8, 1994

§ 102(e) Date: Dec. 8, 1994

[87] PCT Pub. No.: WO93/25550

PCT Pub. Date: Dec. 23, 1993

[30] Foreign Application Priority Data

Jun. 9, 1992 [HU] Hungary ................ 19 11/92

[51] Int. Cl.⁶ .............. C07D 401/14; C07D 403/14; A61K 31/55; A61K 31/505

[52] U.S. Cl. .............. 514/218; 544/295; 544/60; 544/125; 514/252; 514/233.2; 514/228.2; 540/575; 540/467; 540/488

[58] Field of Search ............ 544/295, 60, 125; 540/575, 467, 488; 514/218, 252, 295, 233.2, 228.2

[56] References Cited

U.S. PATENT DOCUMENTS 4,547,505 10/1985 Cepen et al. .............. 514/255
5,099,019 3/1992 McCall et al. .............. 544/295

OTHER PUBLICATIONS

Fessenden et al., Organic Chemistry, 2nd ed., 1982, pp. 616–617.

*Primary Examiner*—Matthew V. Grumbling

*Attorney, Agent, or Firm*—Herbert Dubno; Jonathan Myers

[57] ABSTRACT

The invention relates to novel eburnamenine derivatives of formula (I):

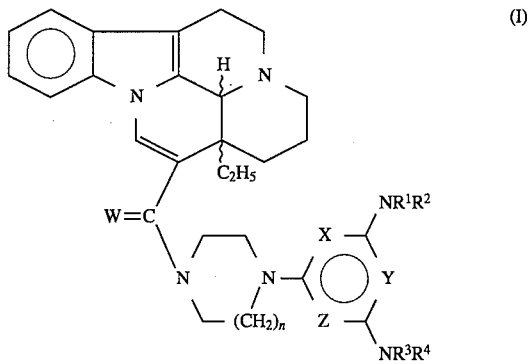

wherein $R^1$ and $R^2$ as well as $R^3$ and $R^4$, independently from each other, stand for hydrogen, $C_{2-6}$alkyl group, $C_{2-6}$alkenyl group; or a $C_{3-10}$alicyclic group involving 1 to 3 rings, and this latter group may be substituted by a $C_{1-6}$alkyl or $C_{2-6}$alkenyl group; or $R^1$ and $R^2$ and/or $R^3$ and $R^4$, together with the adjacent nitrogen atom and optionally with an additional oxygen or nitrogen atom, form a 4- to 6-membered, saturated or unsaturated cyclic group which may be substituted by a $C_{1-6}$alkyl or $C_{2-6}$alkenyl group; two of X, Y and Z are nitrogen whereas the third of them means a methine group; n is 1 or 2; W means oxygen or two hydrogen atoms; and the wavy line means $\alpha$-/$\alpha$-, $\alpha$-/$\beta$- or $\beta$-/$\alpha$- steric position, as well as their acid addition salts and solvates. The invention further relates to pharmaceutical compositions containing the above compounds as well as a process for preparing the compounds of formula (I). The compounds of formula (I) possess antioxidant effect and therefore, they are useful for inhibiting the peroxidation of lipids occurring in mammals (including human).

4 Claims, No Drawings

BIOLOGICALLY ACTIVE EBURNAMENINE DERIVATIVES, PHARMACEUTICAL COMPOSITIONS CONTAINING THEM AND PROCESS FOR PREPARING SAME

FIELD OF THE INVENTION

This is the National Stage of PCT/HU92/00036, filed Jun. 8, 1993.

The invention relates to novel biologically active eburnamenine derivatives of the formula

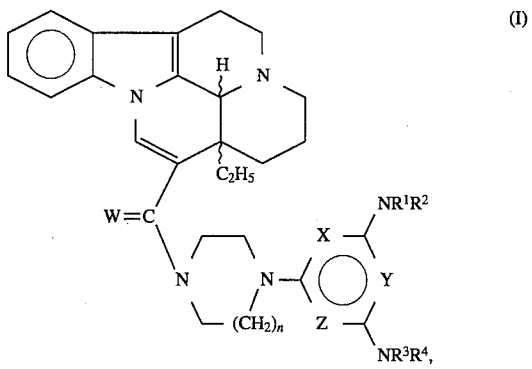

wherein
- $R^1$ and $R^2$ as well as $R^3$ and $R^4$, independently from each other, stand for hydrogen, $C_{2-6}$alkyl group, $C_{2-6}$-alkenyl group; or a $C_{3-10}$alicyclic group containing 1 to 3 rings, and this latter group may be substituted by a $C_{1-6}$alkyl or $C_{2-6}$alkenyl group; or
- $R^1$ and $R^2$ and/or $R^3$ and $R^4$, together with the adjacent nitrogen atom and optionally with an additional oxygen or nitrogen atom, form a 4- to 6-membered, saturated or unsaturated cyclic group which may be substituted by a $C_{1-6}$alkyl or $C_{2-6}$alkenyl group;
- two of X, Y and Z are nitrogen whereas the third of them means a methine group;
- n is 1 or 2;
- W means oxygen or two hydrogen atoms; and the wavy line means $\alpha/\alpha$-, $\alpha$-/$\beta$- or $\beta$-/$\alpha$-steric position, as well as their acid additions salts, solvates and pharmaceutical compositions containing these compounds. Furthermore, the invention relates to a process for the preparation of the above compounds and to a method for inhibiting the peroxidation of lipids in mammals.

In the forthcoming formulae the eburnamenin-14-yl group will hereinafter be abbreviated "EBU"; thus any reference to the meaning of the wavy line relates to said line being present in the partial formula "EBU".

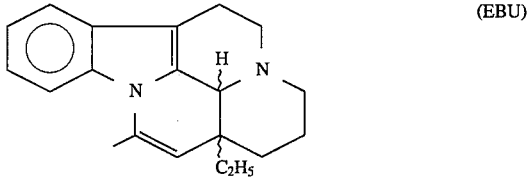

BACKGROUND OF THE INVENTION

The compounds of the formula (I) according to the invention are new and possess a significant antioxidant (lipid peroxidation-inhibiting) effect. Thus, they are therapeutically useful.

There are a high number of pathologic processes known in the case of which extremely reactive free oxygen radicals ($O_2^{-2}$) are accumulated. The formation of these free radicals leads to the oxidation of unsaturated fatty acids (lipid peroxidation) which are important components of the cell membranes. This is a less specific, cell-destroying process, altering or damaging the biomolecules. In this process, functions of various levels of cells, organs or the whole organism may suffer injuries.

Free radical reactions likely play a causal role in the pathogenesis of ischaemia-induced injuries such as ischaemic intestinal diseases, myocardial ischaemia, haemorrhagic shock, cerebrovascular function disturbances accompanied by ischaemia and renal ischaemia [R. J. Korthuis et al.: "Physiology of Oxygen Radicals", Chapter 17, pages 217–249 (1986)].

Due to their lipid peroxidation-inhibiting effect, antioxidative compounds assure protection against injuries induced by free radicals under ischaemic, hypoxic conditions. Thus, antioxidants as antiischaemic and antihypoxic compounds can be used for the treatment of such clinical pictures.

It can be considered to be proven that free radical reactions play a partial role in the development of symptoms of diseases of the connective tissues and a primary aetiological role in rheumatoid arthritis [J. Lunec et al.: "Cellular Antioxidant Defense Mechanisms", Chapter 33, pages 143–159 (1988) (CRC Press Inc., Boca Raton, Fla., 1988)].

There are several hepatotoxic substances known, the liver-damaging effect of which is presumably a consequence of pathologic free radical reactions. Thus, antioxidative compounds may provide protection against acute and chronic diseases of the liver [J. Fehér and A. Vereckei: "The Importance of Free Radical Reactions in Medicine" (in Hungarian), pages 99–104 (Editory Medicina, Budapest, 1985)].

It has essentially been proven that free radical reactions play a role in several haematologic clinical pictures such as sickle-cell anaemia and beta-thalassaemia (Mediterranean anaemia).

Due to the diminished defense ability, $O_2$ therapy or phototherapy, respectively, may further increase the risk of oxidative injuries in the cases of newburn or premature infants. The use of some antioxidants proved to be favorable in the treatment of such clinical pictures.

Lipid peroxidation occurring as a consequence of injuries is a secondary process. Some cells are immediately destroyed by the injury, which then extends also to the surrounding cells in the next following hours. This is also caused by free oxygen radicals which attack the lipid layer of the cell membrane and can eventually lead to cell death by injuring the membrane and releasing hydrogen peroxide. Lipid peroxidation-inhibiting compounds are capable to prevent this secondary process. Thus, they can be used for stopping degenerative processes occurring as a consequence of cephalic and spinal injuries. Compounds having such an effect can be utilized also in the treatment of Alzheimer's disease, muscular dystrophy and the like.

The importance of lipid peroxidation-inhibiting compounds is supported also by the great number of the most recent literature data, patent applications and scientific publications.

In the published PCT patent application No. WO 87/01706, mainly the preparation of aminosteroids is described, where an amino group is bound to the terminal carbon atom of the $C_{17}$ side chain. Double bond(s) is (are) present in position(s) 4 or 1,4 of ring A of the steroid skeleton whereas an oxo or hydroxyl group in position 3, an α- or β-alkyl group or halogen in position 6, mainly an α-hydroxyl group in position 11, an α- or β-methyl group in position 16 and a double bond in position 9(11) are present. The ring A of the steroid skeleton may be saturated or aromatic, too. A few 21-aminosteroids are also described, wherein the double bond takes place in position 17(20). In most cases, the disubstituted pyrimidine, triazine or pyridine cycle is connected through a piperazinyl group to position 21 of the compounds according to this publication. Among the compounds published 16α-methyl-21-{4-[2,4-bis(pyrrolidino)-6-pyrimidinyl]-1-piperazinyl}-pregna-1,4,9(11)-triene-3,20-dione methanesulfonate (tirilazad mesylate) is in the second stage of clinical trials at present.

Similarly, the synthesis of lipid peroxidation-inhibiting compounds containing asteroid skeleton is described in the published PCT patent application No. WO 87/07895, where mainly the preparation of steroid amino esters and corticoid amino esters, especially 17-amino esters, 11,17-bis(amino) esters, 3,17-bis(amino) esters, 11-amino esters and 3-amino esters is discussed. According to this patent application the above derivatives can be used for inhibiting the lipid peroxidation occurring as a consequence of spinal, cephalic and other injuries. The structure of amino substituents is similar to that described in the preceding publication.

The preparation of novel amino-9,10-secosteroids is described in the published PCT patent application No. WO 88/07527. The amino substituent is connected to the terminal carbon atom of the $C_{17}$ side chain of the secosteroid. The amino substituents are the same as those described in the preceding publications.

The synthesis of lipid peroxidation-inhibiting compounds is described also in the published. European patent applications Nos. 0,389,368, 0,389,369 and 0,389,370 as follows.

The preparation of corticoid-type 21-aminosteroids is disclosed in the application No. 0,389,368. For example, a 4-[2,5-bis(diethylamino)-6-pyridinyl]piperazinyl group may be bound to the $C_{21}$ carbon atoms. The steroid skeleton contains one or two double bond(s) in the ring A, whereas the substituents being characteristic of the corticoids may be present in positions 6, 9, 11, 16 and 17. A double bond may be present in position 9(11), too.

The synthesis of amine derivatives of 3-oxo-19-nor-steroids is described in the patent application No. 0,3S9,370 wherein 17β-hydroxy-11β-(4-dimethylaminophenyl)-17α-{3-[4-(2, 6-bis-(pyrrolidino)-4-pyrimidinyl)-1-piperazinyl]-1-propynyl} -estra-4,9-dien-3-one, 17β-hydroxy-11β-(4-dimethylaminophenyl)-17α-{3-[4-(5, 6-bis-(diethylamino)-2-pyridyl)-1-piperazinyl]-1-propynyl}-estra-4,9-dien-3-one, 17β-hydroxy-11β-(4-dimethylaminophenyl)-17α-{3-[4-(3, 6-bis-(diethylamino)-2-pyridyl)-1-piperazinyl]-1-propynyl}-estra-4,9-dien-3-one, 17β-hydroxy-11β-(4-dimethylaminophenyl)-17α-{3-[4-[2, 6-bis-(1-pyrrolidinyl)-4-pyrimidinyl]-1-piperazinyl]-1-propenyl}estra-4,9-dien-3-one and 17β-hydroxy-11β-(4-dimethylaminophenyl)-17α-{3-[4-[2, 6-bis-(pyrrolidino)-4-pyrimidinyl]-1-piperazinyl]-1-propyl}-estra -4,9-dien-3-one are named as compounds prepared.

In the patent application Ser. No. 0,389,369 the synthesis of aminosteroid derivatives containing an androstane skeleton is described, which similarly possess a lipid peroxidation-inhibiting effect. Such compounds are e.g. 11β,17β-dihydroxy-17α-{3-[4-[2,6-bis(pyrrolidino)-4-pyrimidinyl)-1-piperazinyl]-1-propynyl}-androsta-4,6-dien-3-one, 11β, 17β-dihydroxy-6-methyl-17α-{3-[4-[2,6-bis(pyrrolidino)-4-pyrimidinyl] -1-piperazinyl]-1-propynyl}-andostra-1,4,6-trien-3-one, 11β,17β-dihydroxy-6-methyl-17α-{3-[4-[5,6-bis(diethylamino)-2-pyridyl]-1-piperazinyl]-1-propynyl}-andostra-1,4,6-trien-3-one and 11β,17β-dihydroxy-6-methyl-17α-{3-[4-[3,6-bis(diethylamino)-2-pyridyl]-1-piperazinyl]-1-propynyl}-andostra-1,4,6-trien-3-one.

In the published European patent application No. 0,156, 643 mainly the preparation of water-soluble corticosteroid derivatives is reported, the main characteristic of which is that a hydroxyl group or an esterified hydroxyl group stands in the α-position or a double bond is present in position 9(11). From the compounds discussed, sodium [17α-hydroxy-11α-(2,2-dimethylpropylcarbonyloxy)-pregna-1,4-dien-3,20-dion-21-yl]succinate is considered to be the most active lipid peroxidation-inhibiting compound.

In the published PCT application No. WO 91/11453 bis-("amino")pyrimidinyl-piperazinyl derivatives containing an oxygen function in position 5 are disclosed, in the case of which asteroid molecule or a 3,4-dihydro-6-hydroxy-2,5,7,8-tetramethyl-2H-1-benzopyran-2-ylmethyl group or a derivative thereof may be connected to the nitrogen atom in position 1 of the piperazine moiety. Alkyl-substituted 5-hydroxypyrimidine derivatives are also described in this patent application.

Logically, the research in the field of lipid peroxidation-inhibiting compounds has been extended also to the investigation of amine derivatives containing no steroid skeleton. Thus, e.g. in the published PCT patent application No. WO 88/08424 the preparation of novel aromatic and aliphatic bicyclic amine, cycloalkylamine, quinone-amine, amino ether and bicyclic amino ether derivatives are described, which may be useful for the healing of cephalic and spinal injuries. Of the derivatives described 2-{[4-[2,6-bis(pyrrolidino)-4-pyrimidinyl]-1-piperazinyl]-methyl}-3,4-dihydro-2,5,7,8-tetramethyl-2H-1-benzopyran-6-ol dihydrochloride has been subjected to detailed investigations.

OBJECT OF THE INVENTION

The object of the present invention is developing new compounds showing a higher biological efficacy and/or lower toxicity, in comparison to those known in the art because the properties mentioned result in a more preferable therapeutical utilization than that achieved by the known drugs.

SUMMARY OF THE INVENTION

Surprisingly, it has been found that eburnamenine derivatives of the formula (I) possess the desired excellent lipid peroxidation-inhibiting effect.

The novel eburnamenine derivatives of the formula (I) can be prepared by a) reacting an eburnameninecarbonyl chloride of the formula

or the hydrochloride thereof with a piperazine derivative of the formula

reacting the obtained 1-(eburnameninecarbonyl)piperazine of the formula

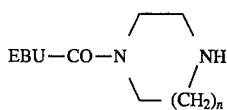
(IV)

with 2,4,6-trichloropyrimidine, separating the thus obtained isomeric mixture containing 1-eburnameninecarbonyl-4-(4,6-dichloropyrimidin-2-yl)piperazine of the formula

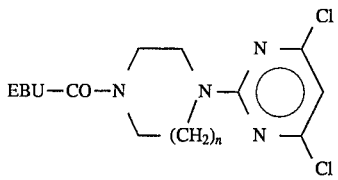
(IIIa)

and 1-eburnameninecarbonyl-4-(2,4-dichloropyrimidin-6-yl)piperazine of the formula

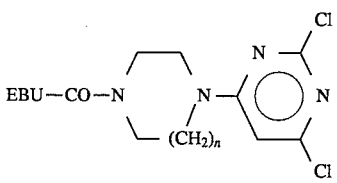
(IIIb)

to the individual isomers, then reacting about 1 mole of 1-eburnameninecarbonyl-4-(4,6-dichloropyrimidin-2-yl)piperazine of the formula (IIIa) with about 2 moles of an amine of the formula $HNR^1R^2$ in one or two step(s) to obtain eburnamenine derivatives of the formula (I), wherein $R^1$ and $R^2$ are the same as $R^3$ and $R^4$, X and Z means nitrogen, Y is a methine group, and n as well as the wavy line are as defined above; or reacting about 1 mole of 1-eburnameninecarbonyl-4-(4,6-dichloropyrimidin-2-yl)piperazine of the formula (IIIa) with about 1 mole of an amine of the formula $HNR^1R^2$, then reacting the obtained 1-eburnameninecarbonyl-4-(4-amino-6-chloropyrimidin-2-yl)piperazine of the formula

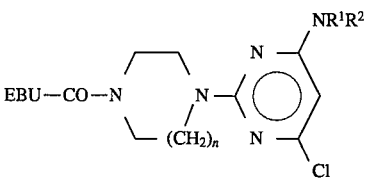
(IIa)

with an amine of the formula $HNR^3R^4$ to give eburnamenine derivatives of the formula (I), wherein $R^1$ and $R^2$ are different from $R^3$ and $R^4$, X and Z mean nitrogen, Y is a methine group, and n as well as the wavy line are as defined above; or reacting about 1 mole of 1-eburnameninecarbonyl-4-(2,4-dichloropyrimidin-6-yl)piperazine of the formula (IIIb) with about 2 moles of an amine of the formula $HNR^1R^2$ in one or two step(s) to obtain eburnamenine derivatives of the formula (I) wherein $R^1$ and $R^2$ are the same as $R^3$ and $R^4$, X and Y mean nitrogen, Z is a methine group, and n as well as the wavy line are as defined above; or reacting about 1 mole of 1-eburnameninecarbonyl-4-(2,4-dichloropyrimidine-6-yl)piperazine of the formula (IIIb) with about 1 mole of an amine of the formula $HNR^1R^2$, then separating the obtained isomeric mixture containing 1-eburnameninecarbonyl-4-(2-amino-4-chloropyrimidin-6-yl)piperazine of the formula

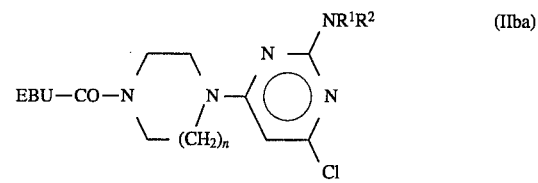
(IIba)

and 1-eburnameninecarbonyl-4-(4-amino-2-chloropyrimidin-6-yl)piperazine of the formula

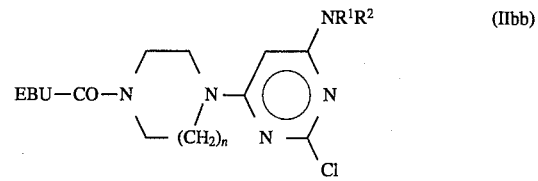
(IIbb)

to the individual isomers and reacting about 1 mole thereof with about 1 mole of an amine of the formula $HNR^3R^4$, wherein $R^3$ and $R^4$ are different from $R^1$ and $R^2$, to give eburnamenine derivatives of the formula (I), wherein $R^1$ and $R^2$ are different from $R^3$ and $R^4$, X and Y mean nitrogen, Z is a methine group, or Z and Y mean nitrogen and X is a methine group, and n as well as the wavy line are as defined above; or a1) reacting a 1-(eburnameninecarbonyl)piperazine of the formula (IV), wherein n and the wavy line are as defined above, with 2,4,6-trichloropyrimidine, separating the isomeric mixture containing 1-eburnameninecarbonyl- 4-(4,6-dichloropyrimidine-2-yl)piperazine of the formula (IIIa) and 1-eburnameninecarbonyl-4-(2,4-dichloropyrimidin-6-yl)piperazine of the formula (IIIb), wherein n and the wavy line are as defined above, to the individual isomers, then reacting 1 mole of the obtained 1-eburnameninecarbonyl-4-(4,6-dichloropyrimidin-2-yl) piperazine of the formula (IIIa) with 2 moles of an amine of the formula $HNR^1R^2$, wherein $R^1$ and $R^2$ are the same as $R^3$ and $R^4$, in one or two step(s), to give eburnamenine derivatives of the formula (I), wherein $R^1$ and $R^2$ are the same as $R^3$ and $R^4$, X and Z mean nitrogen, Y is a methine group, and as well as the wavy line are as defined above; or reacting 1 mole of 1-eburnameninecarbonyl-4-(4,6-dichloropyrimidin- 2-yl) piperazine of the formula (IIIa) with 1 more of an amine of the formula $HNR^1R^2$, wherein $R^1$ and $R^2$ are different from $R^3$ and $R^4$, to obtain eburnamenine derivatives of the formula (I), wherein $R^1$ and $R^2$ are different from $R^3$ and $R^4$, X and Z mean nitrogen, Y is a methine group, and n as well as the wavy line are as defined above, then reacting the obtained 1-eburnameninecarbonyl-4-(4-amino-6-chloropyrimidin-2-yl)piperazine of the formula (IIa), wherein $R^1$, $R^2$, n and the wavy line are as defined above, with an amine of the formula $HNR^3R^4$, wherein $R^3$ and $R^4$ are different from $R^1$ and $R^2$, to obtain eburnamenine derivatives of the formula (I), wherein $R^1$ and $R^2$ are different from $R^3$ and $R^4$, X and Z mean nitrogen, Y is a methine group and n as well as the wavy line are as defined above; or reacting 1 mole of 1-eburnameninecarbonyl-4-(2,4-dichloropyrimidin-6-yl) piperazine of the formula (IIIb) with 2 moles of an amine of the formula $HNR^1R^2$, wherein $R^1$ and $R^2$ are the same as $R^3$ and $R^4$, in one or two step(s), to give eburnamenine derivatives of the formula (I), wherein $R^1$ and $R^2$ are the same as $R^3$ and $R^4$, X and Y mean nitrogen, Z is a methine group, and n as well as the wavy line are as defined above; or reacting 1 mole of 1-eburnameninecarbonyl-4-(2,4-dichloropyrimidine-6-yl)piperazine of the formula (IIIb) with 1 mole of an amine of the formula $HNR^1R^2$, wherein $R^1$ and $R^2$ are different from $R^3$ and $R^4$, then separating the isomeric mixture containing 1-eburnameninecarbonyl-4-(2-amino-4-chloropyrimidin-6-yl)piperazine of the formula (IIba) and 1-eburnameninecarbonyl-4-(4-amino-2-chloropyrimidin-6-yl)piperazine of the formula (IIbb), wherein $R^1$, $R^2$, n and the wavy line are as defined above, to the individual isomers and reacting 1 mole thereof with 1 mole of an amine of the formula $HNR^3R^4$, wherein $R^3$ and $R^4$ are different from $R^1$ and $R^2$, to give eburnamenine derivatives of the formula (I), wherein $R^1$ and $R^2$ are different from $R^3$ and $R^4$, X and Y mean nitrogen and Z is a methine group or Z and Y mean nitrogen and X is a methine group, and n as well as the wavy line are as defined above; or a2a) reacting about 1 mole of 1-eburnameninecarbonyl-4-(4,6-dichloropyrimidin-2-yl)piperazine of the formula (IIIa), wherein n and the wavy line are as defined above, with about 2 moles of an amine of the formula $HNR^1R^2$, wherein $R^1$ and $R^2$ are the same as $R^3$ and $R^4$, in one or two step(s) to obtain eburnamenine derivatives of the formula (I), wherein $R^1$ and $R^2$ are the same as $R^3$ and $R^4$, X and Z mean nitrogen, Y is a methine group, and n and the wavy line are as defined above; or a2b) reacting about 1 mole of 1-eburnameninecarbonyl-4-(4,6-dichloropyrimidin-2-yl)piperazine of the formula (IIIa), wherein n and the wavy line are as defined above, with about 1 mole of an amine of the formula $HNR^1R^2$, wherein $R^1$ and $R^2$ are different from $R^3$ and $R^4$, then reacting the obtained 1-eburnameninecarbonyl-4-(4-amino-6-chloropyrimidin-2-yl)piperazine of the formula (IIa), wherein $R^1$, $R^2$, n and the wavy line are as defined above, with an amine of the formula $HNR^3R^4$, wherein $R^3$ and $R^4$ are different from $R^1$ and $R^2$, to obtain eburnamenine derivatives of the formula (I), wherein $R^1$ and $R^2$ are different from $R^3$ and $R^4$, X and Z mean nitrogen, Y is a methine group and n as well as the wavy line are as defined above; or a2c) reacting about 1 mole of 1-eburnameninecarbonyl-4-(2,4-dichloropyrimidin-6-yl)piperazine of the formula (IIIb), wherein n and the wavy line are as defined above, with about 2 moles of an amine of the formula $HNR^1R^2$, wherein $R^1$ and $R^2$ are the same as $R^3$ and $R^4$, in one or two step(s), to obtain eburnamenine derivatives of the formula (I), wherein $R^1$ and $R^2$ are the same as $R^3$ and $R^4$, X and Y mean nitrogen, Z is a methine group, and n and the wavy line are as defined above; or a2d) reacting about 1 mole of 1-eburnameninecarbonyl-4-(2,4-dichloropyrimidin-6-yl)piperazine of the formula (IIIb), wherein n and the wavy line are as defined above, with about 1 mole of an amine of the formula $HNR^1R^2$, wherein $R^1$ and $R^2$ are different from $R^3$ and $R^4$, then separating the obtained isomeric mixture containing 1-eburnameninecarbonyl-4-(2-amino-4-chloropyrimidin-6-yl)piperazine of the formula (IIba) and 1-eburnameninecarbonyl-4-(4-amino-2-chloropyrimidin-6-yl)piperazine of the formula (IIbb), wherein $R^1$, $R^2$, n and the wavy line are as defined above, to the individual isomers and then reacting about 1 mole thereof with about 1 mole of an amine of the formula $HNR^3R^4$, wherein $R^3$ and $R^4$ are different from $R^1$ and $R^2$, to give eburnamenine derivatives of the formula (I), wherein $R^1$ and $R^2$ are different from $R^3$ and $R^4$, X and Y mean nitrogen and Z is a methine group or Z and Y mean nitrogen and X is a methine group, n and the wavy line are as defined above; or a3a) reacting a 1-eburnameninecarbonyl-4-(4-amino-6-chloropyrimidin-2-yl)piperazine of the formula (IIa), wherein $R^1$, $R^2$, n and the wavy line are as defined above with an amine of the formula $HNR^3R^4$, wherein $R^3$ and $R^4$ are as defined above, to obtain eburnamenine derivatives of the formula (I), wherein X and Z mean nitrogen, Y is a methine group, $R^1$, $R^2$, $R^3$, $R^4$, n and the wavy line are as defined above; or a3b) reacting a 1-eburnameninecarbonyl-4-(2-amino-4-chloropyrimidine-6-yl)piperazine of the formula (IIba), wherein $R^1$, $R^2$, n and the wavy line are as defined above with an amine of the formula $HNR^3R^4$, wherein $R^3$ and $R^4$ are as defined above, to obtain eburnamenine derivatives of the formula (I), wherein X and Y mean nitrogen, Z is a methine group, $R^1$, $R^2$, $R^3$, $R^4$, n and the wavy line are as defined above; or a3c) reacting a 1-eburnameninecarbonyl-4-(4-amino-2-chloropyrimidin-6-yl)piperazine of the formula (IIbb), wherein $R^1$, $R^2$, n and the wavy line are as defined above, with an amine of the formula $HNR^3R^4$, wherein $R^3$ and $R^4$ are as defined above, to give eburnamenine derivatives of the formula (I), wherein Z and Y mean nitrogen, X is a methine group, $R^1$, $R^2$, $R^3$, $R^4$, n and the wavy line are as defined above; or ba) reacting a 1-(eburnameninecarbonyl)piperazine of the formula (IV) with a 2-amino-4,6-dichloropyrimidine of the formula

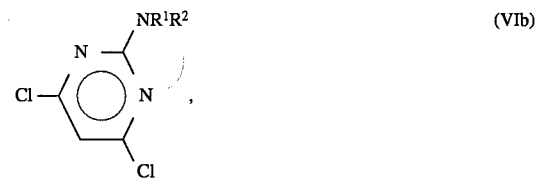

(VIb)

then reacting the obtained 1-eburnameninecarbonyl-4-(2-amino-4-chloropyrimidin-6-yl)piperazine of the formula (IIba) with an amine of the formula $HNR^3R^4$; or bb) reacting a 1-(eburnameninecarbonyl)piperazine of the formula (IV) with a 4-amino-2,6-dichloropyrimidine of the formula

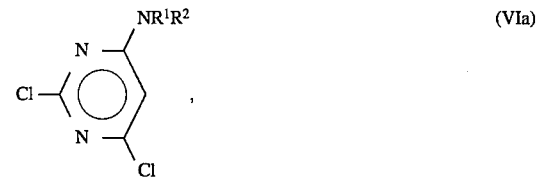

(VIa)

then separating the obtained isomeric mixture containing 1-eburnameninecarbonyl-4-(4-amino-6-chloropyrimidine-2- yl)piperazine of the formula (IIa) and 1-eburnameninecarbonyl-4-(4-amino-2-chloropyrimidin-6-yl)piperazine of the formula (IIbb) to the individual isomers and reacting about 1 mole thereof with about 1 mole of an amine of the formula $HNR^3R^4$; or ca) reacting a 1-(eburnameninecarbonyl)piperazine of the formula (IV) with a 4,6-diamino-2-chloropyrimidine of the formula

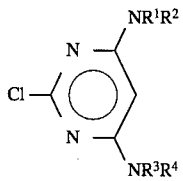
(VIIa)

or cb) reacting a 1-(eburnameninecarbonyl)piperazine of the formula (IV) with a 2,4-diamino-6-chloropyrimidine of the formula

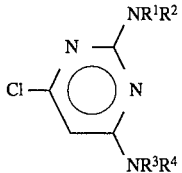
(VIIb)

or da) reacting an eburnameninecarbonyl chloride of the formula (V) or a hydrochloride salt thereof with a 4-(4-amino-6-chloropyrimidin-2-yl)piperazine of the formula

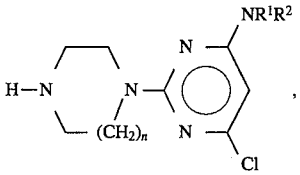
(VIIIa)

then reacting the obtained 1-eburnameninecarbonyl-4-(4-amino-6-chloropyrimidin-2-yl)piperazine of the formula (IIa) with an amine of the formula $HNR^3R^4$; or db) reacting an eburnameninecarbonyl chloride of the formula (V) or a hydrochloride salt thereof with a 4-(4-amino-2-chloropyrimidin-6-yl)piperazine of the formula

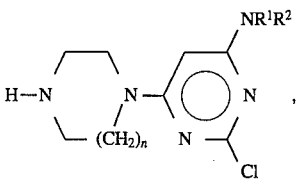
(VIIIbb)

then reacting the obtained 1-eburnameninecarbonyl-4-(4-amino-2-chloropyrimidin-6-yl)piperazine of the formula (IIbb) with an amine of the formula $HNR^3R^4$; or dc) reacting an eburnameninecarbonyl chloride of the formula (V) or a hydrochloride salt thereof with a 4-(2-amino-4-chloropyrimidin-6-yl)piperazine of the formula

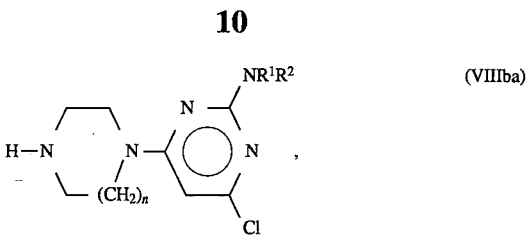
(VIIIba)

then reacting the obtained 1-eburnameninecarbonyl-4-(2-amino-4-chloropyrimidin-6-yl)piperazine of the formula (IIba) with an amine of the formula $HNR^3R^4$; or e) reacting an eburnameninecarbonyl chloride of the formula (V) or a hydrochloride salt thereof with a 4-(diaminopyrimidinyl)piperazine of the formula

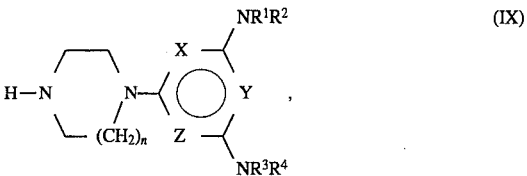
(IX)

and, if desired, reducing a thus obtained eburnamenine derivative of the formula (I) containing an oxo group as W, and/or converting an eburnamenine derivative of the formula (I) obtained as the free base to an acid addition salt by reacting the free base with an acid, and/or liberating the free base from an obtained salt of an eburnamenine derivative of the formula (I) and/or transforming an obtained eburnamenine derivative of the formula (I) to a solvate thereof.

The reaction of an eburnameninecarbonyl chloride or its hydrochloride salt of the formula (V) with a piperazine derivative of the formula (X) is suitably carried out by dissolving about 16 moles of piperazine derivative (calculated for 1 mole of "acyl chloride") in methylene chloride and dropwise adding the solution of the "acyl chloride" to the above solution at −50° C. After the dropwise addition the cooling of the reaction mixture is stopped, the reaction mixture is allowed to warm to room temperature, saturated sodium hydrogen carbonate solution is added and then the mixture is stirred for 10 minutes. After separating the organic phase is thoroughly washed with water, dried and subjected to chromatography on a silica gel column, then the product obtained is purified by recrystallization.

The reaction of a 1-(eburnamenine-14-carbonyl)piperazine of the formula (IV) with 2,4,6-trichloropyrimidine is preferably carried out by dissolving the piperazine derivative in tetrahydrofuran and then dropwise adding at 0° C. 2,4,6-trichloropyrimidine, diluted with tetrahydrofuran, thereto. The reaction mixture is stirred at room temperature for 12 hours, then evaporated to dryness. After distributing the evaporation residue between chloroform and aqueous sodium hydroxide solution the organic phase is washed with water, dried and evaporated. The residue is subjected to chromatography on a silica gel column in order to separate the isomers of the formulae (IIIa) and (IIIb).

The reaction of the isomeric 1-(eburnamenine-14-carbonyl)-4-(dichloropyrimidinyl)piperazine derivatives of the formula (IIIa) and (IIIb), respectively, with amines of the formula $HNR^1R^2$, e.g. pyrrolidine, 1-aminoadamantane, 1-amino-1,1-dimethylethane, 1-amino-2,2-dimethylpropane, cyclopentylamine or the like is carried out at a temperature depending on the reactivity of the amine. This reaction is performed e.g. with pyrrolidine below 10° C. whereas a temperature of at least 80° to 100° C. is used in the reaction with 1-aminoadamantane. After evaporation the residue is distributed between a halogenated solvent, preferably chloroform, and aqueous sodium hydroxide solution. After separation the organic phase is washed with water, dried and evaporated. The thus obtained 1-(eburnamenine-14-carbonyl)-4-(aminochloropyrimidinyl)piperazine isomers are separated on a silica gel column and purified by recrystallization.

The 1-(eburnamenine-14-carbonyl)-4-(aminochloropyrimidinyl)piperazine isomers of formulae (IIa), (IIba) and (IIbb), respectively, are reacted with an amine of the formula $HNR^3R^4$, which is identical to or different from the amine used in the preceding step. This reaction is carried out at a temperature and for a time depending on the reactivity of the amines. For example, in the case of pyrrolidine, boiling for about 5 hours is required. After completion of the reaction, the excess amine is removed by distillation and the residue is distributed between chloroform and aqueous sodium hydroxide solution. After separation the organic phase is washed with water, dried and evaporated. The obtained compounds of the formula (I) can be recrystallized e.g. from acetonitrile.

Alternatively, according to the invention the isomeric 1-(eburnamenine-14-carbonyl)-4-(dichloropyrimidinyl)piperazines of the formula (IIIa) or (IIIb), respectively, may be reacted with the amines of the formula $HNR^1R^2$ or $HNR^3R^4$, respectively, in a single step. Suitably, the eburnamenine derivatives are suspended or dissolved in the primary or secondary amine used as reactant and the mixture is reacted at the boiling temperature. This reaction can be performed e.g. with pyrrolidine by boiling for 5 hours. After the reaction has become complete, the excess amine, e.g. pyrrolidine, is distilled off and the residue is purified as described above.

If 1-(eburnamenine-14-carbonyl)-4-(dichloropyrimidinyl)piperazine cannot be dissolved in the amine of the formula $HNR^1R^2$ or $HNR^3R^4$ at the boiling point thereof, a solvent having a higher boiling point, e.g. n-butanol, is used as solubilizing agent.

Alternatively, a 1-(eburnamenine-14-carbonyl)piperazine of the formula (IV) can be reacted with an aminodichloropyrimidine of the formula (VIa) or (VIb), respectively, and then the obtained 1-(eburnamenine-14-carbonyl)-4-(aminochloropyrimidinyl)piperazine of the formula (IIa), (IIba) or (IIbb), respectively, can be reacted with an amine of the formula $HNR^3R^4$. This process is conveniently carried out by dissolving the 1-(eburnamenine-14-carbonyl)piperazine derivative of the formula (IV) as well as the aminodichloropyrimidine of the formula (VIa) or (VIb), respectively, e.g. in acetonitrile, then boiling the reaction mixture in the presence of potassium carbonate for about 40 hours while vigorously stirring. After termination of the reaction and evaporating the solvent the residue is distributed between chloroform and water. After separating, the organic phase is washed with water, dried and evaporated. The residue is purified by recrystallization. The thus obtained 1-(eburnamenine- 14-carbonyl)-4-(aminochloropyrimidinyl)piperazine derivatives of the formula (IIa), (IIba) or (IIbb), respectively, are reacted with the amines of the formula $HNR^3R^4$ under the reaction conditions described above.

Alternatively, a 1-(eburnamenine-14-carbonyl)piperazine of the formula (IV) may be reacted with a diaminochloropyrimidine of the formula (VIIa) or (VIIb), respectively. This reaction is suitably carried out by dissolving the 1-(eburnamenine- 14-carbonyl)piperazine derivative and a diaminochloropyrimidine, e.g. 4-chloro-2,6-bis(pyrrolidino)pyrimidine, in N-ethylmorpholine, boiling the reaction mixture under nitrogen for 40 hours and then evaporating under environmental pressure. From the residue the traces of N-ethylmorpholine are removed by adding water and distilling off the water. After distributing the residue between chloroform and water, the organic phase is separated, washed with water, dried and evaporated. The residue is purified by chromatography.

Alternatively, an eburnamenine-14-carbonyl chloride of formula (V) or the hydrochloride salt thereof is reacted with an 1-(aminochloropyrimidinyl)piperazine derivative of the formula (VIIIa), (VIIIba) or (VIIIbb), respectively, and thereafter, the obtained 1-(eburnamenine-14-carbonyl)-4-(aminochloropyrimidinyl)piperazine of the formula (IIa), (IIa), (IIba) or (IIbb), respectively, is reacted e.g. with an amine of the formula $HNR^3R^4$.

This latter process is suitably accomplished, for example, as follows. A solution of the 1-(aminochloropyrimidinyl)piperazine of the formula (VIIIa), (VIIIba) or (VIIIbb), respectively is prepared, in methylene chloride and then potassium carbonate is added to the hydrochloride of eburnamenine- 14-carbonyl chloride of formula (V) at a temperature of −15° C. in small portions. Subsequently, the cooling of the reaction mixture is stopped, its temperature is allowed to warm to room temperature and then water is added. After stirring for about 10 minutes and then separating the phases, the organic solution is washed with water, the solvent is distilled off and the residue is purified by recrystallization. The obtained 1-(eburnamenine-14-carbonyl)-4-(aminochloropyrimidinyl)piperazine of the formula (IIa), (IIba) or (IIbb), respectively, is then reacted with an amine of the formula $HNR^3R^4$ as described above.

The present invention relates also to a process comprising the reaction of an eburnamenine-14-carbonyl chloride of the formula (V) or the hydrochloride thereof with a bis(amino)-(1-piperazinyl)pyrimidine derivative of the formula (IX). According to this process, to a solution containing the bis(amino)-(1-piperazinyl)pyrimidine derivative of the formula (IX) used as reactant in a halogenated solvent, e.g. methylene chloride, the hydrochloride of eburnamenine-14-carbonyl chloride of the formula (V) and then potassium carbonate are added in small portions at a temperature of −15° C. Subsequently, the cooling of the reaction mixture is ceased; it is allowed to warm to room temperature and water is added. After stirring for about 10 minutes the phases are separated, the organic layer is washed with water and after evaporating the solvent the evaporation residue is purified by recrystallization.

If desired, the eburnamenine derivatives of the formula (I), obtained in the preceding processes and containing oxygen as W, can be reduced to eburnamenine derivatives of the formula (I) containing two hydrogen atoms as W; and/or an eburnamenine derivative of the formula (I) obtained in the form of the free base can be transformed to an acid addition salt by reacting it with an appropriate acid; and/or the free base can be liberated from an eburnamenine derivative of the formula (I) obtained in the form of a salt.

The reaction is suitably carried out by dissolving the derivative of the formula (I) containing oxygen as W in anhydrous tetrahydrofuran and adding it dropwise to a solution of lithium aluminum hydride in tetrahydrofuran under an inert gas, e.g. argon, then boiling the reaction mixture for about 3 hours. After the reaction has become complete [according to thin layer chromatography (TLC) analysis], the excess of lithium aluminum hydride as well as the complex formed is decomposed by adding water and aqueous sodium hydroxide solution. The aluminum hydroxide and lithium hydroxide precipitate is filtered off, washed thoroughly with tetrahydrofuran and after evaporating tetrahydrofuran from the filtrate combined with the washings, the residue is purified on a silica gel column by chromatography.

Acid addition salts of the compounds of the formula (I) are formed in a usual manner, e.g. by dissolving any of the compounds of the formula (I) in anhydrous ethanol and adding about 1 or 2 molar equivalent(s) of an acid, e.g. methanesulfonic acid or ethanesulfonic acid, to the above solution. When the salt does not precipitate, ether is added to the alcoholic solution and after compacting the precipitated product is filtered off, dried and, if desired, purified by dissolving and precipitation, or the precipitated product is transformed to the corresponding free base.

In this description and in the claims $C_{2-6}$ alkyl and alkenyl groups are meant to be straight or, preferably, branched chain $C_{2-6}$ groups which are saturated or contain one or more carbon-carbon double bond(s). Such $C_{2-6}$ alkyl and alkenyl groups are exemplified by the ethyl, vinyl, n-propyl, isopropyl, 1-propen-1-yl, 1-propen-2-yl, 1-propen-3-yl, n-butyl, sec-butyl and tert-butyl and butenyl group as well as the various pentyl, pentenyl, hexyl and hexenyl groups. $C_{3-10}$ cycloalkyl groups containing 1 to 3 rings and unsubstituted by $C_{1-3}$ alkyl group, are e.g. cyclobutyl, cyclopentyl, cyclohexyl, cycloheptyl as well as adamantyl groups. These groups may be unsubstituted or may bear one ore more methyl, ethyl or propyl group(s) and substituent(s).

When $R^1$ and $R^2$ and/or $R^3$ and $R^4$ together with the adjacent nitrogen atom and optionally with a further oxygen or nitrogen atom form a saturated or unsaturated cyclic group containing 4 to 6 carbon atoms, optionally substituted by $C_{1-4}$ alkyl or alkenyl group, these cyclic groups may preferably be a pyrrolidino, piperidino, azepino, morpholino, 4,4-ethylenedioxy-1-piperidinyl or 2,2,6,6-tetramethyl-1-piperidinyl group.

The various compounds of formulae (VI), (VII), (VIII) and (IX) used for the preparation of the compounds of the formula (I) or their intermediates, respectively, can be prepared as follows.

For the preparation of various monoamino-dichloropyrimidine derivatives of the formula (VI) 2,4,6-trichloropyrimidine is used as starting material, and it is reacted in an ether-type solvent, e.g. tetrahydrofuran, with a primary or secondary amine at a temperature between −20° C. and 40° C., depending on the reactivity of the amine, for a period of about 30 minutes to several hours. In the case of the sterically hindered 2,2,4,4-tetramethylpiperidine (which can be used as solvent, too), the completion of the reaction lasts for about 50 hours at the boiling point of the reaction mixture. After completion of the reaction the solvent or the reactant (used as a solvent, too) is evaporated, the residue is dissolved in a halogenated solvent, preferably chloroform, and extracted first with aqueous sodium hydroxide solution, then water. After separating, the organic phase is dried, the solvent is evaporated and the 4,6-dichloro-2-aminopyrimidine of the formula (VIa) is separated from the 2,6-dichloro-4-aminopyrimidine derivative of the formula (VIb) on a silica gel column by chromatography. Thereafter, the individual isomers are further purified by recrystallization.

The bis(amino)-chloropyrimidine derivatives of the formula (VIIa) and (VIIb), respectively, are prepared by reacting the corresponding monoamino-dichloropyrimidine derivatives of the formula (VI) with an amine of the formula $HNR^1R^2$ or $HNR^3R^4$, respectively. Similarly to the preparation of compounds of the formula (VI), the reaction conditions are above all determined by the reactivity of the amine of of the formula $HNR^1R^2$ or $HNR^3R^4$ used. Thus, on using pyrrolidine as amine component, the reaction proceeds at room temperature; whereas the reaction with 1-amino-1,1-dimethylethane requires heating at 130° C. for about 15 hours. The interaction with 1-amino-2,2-dimethylpropane can be accomplished under milder conditions: it becomes complete by boiling in isopropanol for about 20 hours. If as amine component the bulky 1-aminoadamantane is used, it reacts by boiling in n-butanol for about 75 hours. The reaction mixtures obtained are worked up as described for the preparation of compounds of the formula (VI).

For preparing the various piperazinyl pyrimidine derivatives of the formula (VIII) the corresponding bis(amino)-chloropyrimidine derivatives of the formula (VII) are employed as starting substances. After being dissolved in a tertiary amine, preferably N-ethylmorpholine, the bis(amino)-chloropyrimidine derivatives of the formula (VII) are boiled with an excess of a piperazine of the formula (X) under nitrogen for about 25 hours. After termination of the reaction N-ethylmorpholine used as solvent and a major part of the piperazine are distilled off, water is added to the residue and distilled off again. After dissolving in chloroform, the residue is washed with aqueous sodium hydroxide solution, then with water. After separation the organic phase is dried and chloroform is evaporated. The residue is purified by chromatography on a silica gel column and optionally the product obtained is recrystallized.

For the preparation of bis(amino)-(1-piperazinyl)pyrimidine derivatives of the formula (IX) e.g. the bis(amino)-chloropyrimidine derivatives of the formula (VII) may be used as starting substances. Suitably, the compounds of the formula (VII) are reacted with an about 5-fold excess of a piperazine of formula (X) by boiling the reactants in ethanol for about 1 hour. After termination of the reaction ethanol is evaporated, the residue is dissolved in chloroform, washed with aqueous sodium hydroxide solution and then with water. After separation the organic phase is dried and the solvent is evaporated. The residue is purified by recrystallization.

Eburnameninecarbonyl chlorides of the formula (V) and their hydrochloride salts used as starting substances in the process of invention are known from the Hungarian patent specification No. 187,733.

The pharmacological effect of the eburnamenine derivatives of the formula (I) was studied as described hereinafter. The antioxidative effect was investigated in an enzymatically-induced lipid peroxidation (NADPH-induced lipid peroxidation) test as well as in a non-enzymatically induced lipid peroxidation ($Fe^{2+}$-induced lipid peroxidation) test.

The antioxidative effect was investigated on microsomes prepared from rat brain [J. Neurochem. 37, pages 422–426 (1981)] and on rat brain homogenate [J. Biol Chem. 262, pages 10438–10440 (1987)].

Inhibition of the NADPH-induced lipid peroxidation in brain microsomes

Male Hannover-Wistar rats with a body weight of 150–250 g were used for the preparation of microsomes. After decapitation, the whole brain of the rat was removed and homogenized in a 10-fold volume of ice-cold 0.25M saccharose solution. The homogenate was centrifuged in a Hitachi CR 26H equipment at 15000×g at 4° C. for 10 minutes, then the supernatant was collected and centrifuged in a Hitachi SCP85H equipment at 78000×g at 4° C. for 60 minutes. After suspending the precipitate in 0.15M potassium chloride solution, the protein content of the obtained solution was determined and then adjusted to 10 mg/ml concentration. The microsome thus obtained was frozen in a dry ice-acetone mixture and stored at −70° C. until use.

The components of the incubation mixtures were: 50 mM tris(hydroxymethyl)aminomethane hydrochloride (pH 6.8), 0.2 mM ferric chloride, 1 mM potassium dihydrogen phosphate, 0.5 mM adenosine-5'-diphosphate, 0.2 mg of microsomes as well as the compound to be tested. The incubation was carried out with a final volume of 1 ml and an incubation time of 20 minutes at a temperature of 37° C. The lipid peroxidation was induced by adding 0.4 mM NADPH (nicotine adenine dinucleotide phosphate, reduced form). (The blank samples did not contain NADPH.) The reaction was stopped by adding 0.375 ml of a stopping solution containing trichloroacetic acid of 40% and 5M hydrochloric acid in a 2:1 ratio. The formation of malondialdehyde was determined by using thiobarbituric acid. After stopping the reaction, 1 ml of 1% thiobarbituric acid solution each was added to the samples, which were then 10 placed in a water bath of about 100° C. for 10 minutes. Subsequently, the samples were centrifuged at 2000×g in a Janetzki K70 apparatus at 4° C. for 10 minutes. The absorbance value of the colored supernatant was measured at 535 nm in a Hitachi 150-20 spectrophotometer. Malondialdehyde bis(diethylacetal) was used as reference compound.

Effect on the $Fe^{2+}$-induced lipid peroxidation in brain homogenate

After decapitating Hannover-Wistar rats weighing 150–220 g each, the whole brain was homogenized in 9 volumes of icecold Krebs-Ringer's buffer [containing 15 mM 4-(2-hydroxyethyl)- 1-(piperazinylethanesulfonic acid (abbreviated: HEPES, pH 7.4), 140 mM sodium chloride, 3.6 mM potassium chloride, 1.5 mM calcium chloride, 0.7 mM magnesium chloride, 1.4 mM potassium dihydrogen phosphate and 10 mM glucose]. Then, the protein content of the solution was determined and adjusted to 10 mg/ml concentration.

After adding the inhibitory agent to be tested in a volume of 5 ml to 200 µl of the homogenate, the incubation mixture was incubated at 37° C. for 20 minutes. The $Fe^{2+}$-induced lipid peroxidation was accomplished by adding 5 µl of 8 mM ferrous diammonium disulfate $[Fe(NH_4)_2(SO_4)_2]$ solution. After passing of the incubation time, the reaction was stopped by adding 1 ml of a stopping solution containing 0.8M hydrogen chloride in trichloroacetic acid solution of 12.5%; then the samples were centrifuged at 2000×g in a Janetzki apparatus at 4° C. for 10 minutes.

To 0.5 ml portion of the supernatant, 1 ml of 1% thiobarbituric acid solution was added, then the samples were placed in a water bath of 100° C. for 20 minutes. The color intensity developed was determined at 535 nm with the aid of a Hitachi 150-20 spectrophotometer by using malondialdehyde bis(diethylacetal) as reference compound.

The $IC_{50}$ values of the compounds were determined on the basis of the concentration/effect correlations thereof and are indicated in Table I.

TABLE I

| | Lipid peroxidation-inhibiting effect | |
|---|---|---|
| Compound No. | Inhibition of the NADPH-induced lipid peroxidation $IC_{50}$ (µM) | Inhibition of the $Fe^{2+}$-induced lipid peroxidation $IC_{50}$ (µM) |
| 1 | 24.2 | 124.0 |
| 2 | 6.2 | 112.0 |
| 3 | 2.4 | 11.4 |
| 4 | 3.1 | 10.3 |
| DL-α-Tocopherol | N.I. | 10.5 |
| Ellagic acid | 47.2 | 51.0 |
| Silymarin | 197.0 | 33.2 |
| Tirilazad mesylate | 121.0 | 135.0 |

Signs and abbreviation used in Table I:
N.I.: no inhibition
1: 1-[(3α,16α)-eburnamenine-14-carbonyl]-4-[2,6-bis(pyrrolidino)- 4-pyrimidinyl]piperazine
2: 1-{[(3α,16α)-eburnamenine-14-yl]methyl}-4-[2,6-bis(pyrrolidino)- 4-pyrimidinyl]piperazine trihydrobromide
3: 1-[(16α)-eburnamenine-14-carbonyl]-4-[2,6-bis(pyrrolidino)- 4-pyrimidinyl]piperazine
4: 1-[(3α)-eburnamenine-14-carbonyl]-4-[2,6-bis(pyrrolidino)- 4-pyrimidinyl]piperazine
Ellagic acid: 4,4',5,5',6,6'-hexahydrodiphenic acid 2,6':2',6-dilactone
Silymarin: 2-[trans-2-(4-hydroxy-3-methoxyphenyl)-3-hydroxymethyl- 1,4-benzodioxan-6-yl]-3,5,7-trihydroxychroman-4-one
Tirilazad mesylate: 16α-methyl-21-{4-[2,4-bis(pyrrolidino)6-pyrimidinyl]-1-piperazinyl}-pregna-1,4,9(11)-trien-3,20-dione methanesulfonate (a compound of the published PCT patent application No. WO 87/01706).

Based on the data of Table I it can be seen that each of the compounds prepared in the various Examples exerts a very strong antioxidant (lipid peroxidation-inhibiting) action.

According to the date of Table I the inhibitory effect of the compounds tested on the NADPH-induced (enzymatically induced) lipid peroxidation is much stronger than that of the reference compounds. It is likely that the compounds exert their antioxidant effect through the NADPH-cytochrom C reductase involved in the reaction. The inhibitory effect of compounds 3 and 4 on the $Fe^{2+}$-induced (non-enzymatically induced) lipid peroxidation reaches the antioxidant activity of the therapeutically used DL-α-tocopherol; whereas they inhibit this process more effectively than the hepatoprotective silymarin or the anticancerogenic ellagic acid. In addition, the antioxidant activity of the compounds 1 and 2 reaches and even exceeds to some extent the lipid peroxidation-inhibiting effect of tirilazad mesylate being under clinical trials at present.

The novel eburnamenine derivatives of the formula (I) are employed for pharmacological purposes alone or in the form of their salts, suitably in formulations commonly used in therapy. These formulations may be solid, liquid or semisolid; filling, diluting, stabilizing, pH- and osmotic pressure-influencing, flavoring, savoring as well as formulation-promoting or formulation-providing additives and auxiliaries commonly used for such preparations can be used for their preparation.

The solid pharmaceutical compositions may be e.g. tablets, dragees, capsules, cachets (cachet power compositions) or powder ampouls useful for the preparation of injections. Liquid compositions are the injectable and infusable compositions, fluid medicines, packing fluids and drops. Ointments, balsams, creams, mixtures to be shaken and suppositories are semisolid compositions.

The pharmaceutical composition is administered to the patient in an amount containing the dose of the active agent required to achieve the desired effect. This dose depends on the grade of the disease, the severity of the pathological condition to be influenced, the weight of the patient, sensitivity of the patient against the active agent, route of the administration and number of daily treatments. The dose of active agent to be used can safely be determined by the physician skilled in the art in the knowledge of the patient to be treated.

For the sake of a simple administration it is suitable if the pharmaceutical compositions comprise dosage units containing the amount of the active agent to be administered once, or a few multiples or a half, third or fourth part thereof. Such dosage units are e.g. tablets which can be provided with grooves promoting the halving or quartering of the tablet to obtain the required amount of the active agent.

The tablets can be coated by a layer insoluble in acidic media in order to assure the release of the active agent content after leaving the stomach. In this way, the tablets become enteric-coated. A similar effect can be achieved also by encapsulating the active agent.

The pharmaceutical compositions containing the active agent according to the invention usually contain 1 to 100 mg of active agent in one dosage unit. Of course, it is also possible that, in some compositions, the amount of the active agent exceeds the upper or lower limits defined above.

The invention also relates to a method for inhibiting the peroxidation of lipids occurring in the organism. This method comprises administering a therapeutically effective amount of an active agent of the formula (I) or a pharmaceutically acceptable acid addition salt or solvate thereof to the patient.

The invention is illustrated in detail by the aid of the following non-limiting Examples.

EXAMPLE 1

Preparation of 1-[(3α,16α)-eburnamenine-14-carbonyl]piperazine

A solution containing 20.0 g (53 mmoles) of (3α,16α)-eburnamenine- 14-carbonyl chloride hydrochloride in 200 ml of methylene chloride is dropwise added at −50° C. to 66.8 g (796 mmoles) of piperazine dissolved in 300 ml of methylene chloride. Thereafter, the cooling of the reaction mixture is stopped, the mixture is allowed to warm to room temperature and 100 ml of saturated sodium hydrogen carbonate solution are added, the mixture is stirred for 10 minutes and then settled. After separation the organic phase is twice washed with 150 ml of water each, then dried and evaporated. The residue is purified by chromatography on a silica gel column. The elution is carried out by using a mixture of chloroform/methanol (98:2→80:20). The product obtained is recrystallized to give the title compound in a yield of 15.82 g (78.8%) m.p.: 185°–198° C.

EXAMPLE 2

Preparation of 1-[(3α,16α)-eburnamenine-14-carbonyl]-4-(4,6-dichloro-2-pyrimidinyl)piperazine and 1-[(3α,16α)-eburnamenine-14-carbonyl]-4-(2,6-dichloro-4-pyrimidinyl)piperazine 0.56 ml (4.87 mmoles) of 2,4,6-trichloropyrimidine diluted with 20 ml of tetrahydrofuran is dropwise added to a solution of 2.0 g (5.12 mmoles) of 1-[(3α,16α)-eburnamenine-14-carbonyl]piperazine in 50 ml of tetrahydrofuran at 0° C. After stirring at room temperature for 12 hours the reaction mixture is evaporated to dryness. The residue is distributed between 100 ml of chloroform and 25 ml of 5% sodium hydroxide solution. After separation the organic phase is dried, evaporated and the evaporation residue is subjected to chromatography on silica gel column. By using a chloroform/methanol mixture (100:0→99:1) as eluent, the less polar 1-[(3α,16α)-eburnamenine-14-carbonyl]-4-(4,6-dichloro-2-pyrimidinyl)piperazine is first obtained in a yield of 0.325 g (12.7%), m.p.: 100°–107° C. (after recrystallization from ether). By further elution the more polar 1-[(3α, 16α)-eburnamenine- 14-carbonyl]-4-(2,4-dichloro-6-pyrimidinyl)piperazine is obtained in a yield of 2.26 g (88.3%), m.p.: 165°–175° C. (after recrystallization from ether).

EXAMPLE 3

Preparation of 4,6-dichloro-2-pyrrolidinopyrimidine and 2,4-dichloro- 6-pyrrolidinopyrimidine 23.7 ml (286.6 mmoles) of pyrrolidine are dropwise added at a temperature of −20° C. to the mixture of 25.0 g (136.3 mmoles) of 2,4,6-trichloropyrimidine and 200 ml of tetrahydrofuran over about 30 minutes. Subsequently, the cooling is stopped, the mixture is stirred for additional 30 minutes and then evaporated. The residue is distributed between 500 ml of chloroform and 50 ml of 10% sodium hydroxide solution. After separation the organic phase is washed 4 times with 150 ml of water each, then dried and evaporated. The residue is subjected to chromatography on a silica gel column. By using a hexane/ethyl acetate mixture of 19:1 ratio as eluent 4,6-dichloro-2-pyrrolidinopyrimidine is obtained which is recrystallized from hexane to give 7.51 g (25.27%) of product, m.p.: 95°–98° C.

$^1$H-NMR (60 MHz, CDCl$_3$) δ ppm: 6.51 (s, 1H, 5-H)

By further elution a more polar product is obtained which is recrystallized from hexane to give 2,4-dichloro-6 -pyrrolidinopyrimidine in a yield of 20.22 g (68.03%), m.p.: 100.5°–103.5° C.

$^1$H-NMR (60 MHz, CDCl$_3$) δ ppm: 6.18 (s, 1H, 5-H)

EXAMPLE 4

Preparation of 4-chloro-6-(1-piperazinyl)-2-pyrrolidinopyrimidine

A solution of 2.0 g (9.17 mmoles) of 4,6-dichloro-2-pyrrolidinopyrimidine and 3.95 g (45.9 mmoles) of piperazine in ethanol is boiled under reflux for 1 hour and then evaporated. The evaporation residue is distributed between 100 ml of chloroform and 100 ml of 1% sodium hydroxide solution. After separation the organic phase is twice washed with 50 ml of water each, then dried and evaporated. After recrystallizing the residue from hexane, the title product is obtained in a yield of 2.25 g (91.6%), m.p. 89°–100° C.

EXAMPLE 5

Preparation of 4-chloro-2-(1-piperazinyl)-6-pyrrolidinopyrimidine

A solution containing 2.0 g (9.17 mmoles) of 2,4-dichloro- 6-pyrrolidinopyrimidine and 3.95 (45.9 mmoles) of piperazine in ethanol is boiled under reflux for 1 hour and then evaporated. The evaporation residue is distributed between 100 ml of chloroform and 100 ml of 1% sodium hydroxide solution. After separation the organic phase is washed twice with 50 ml of water each, then dried and evaporated. The evaporation residue is subjected to chromatography on a silica gel column. By using a 9:1 mixture of chloroform/methanol as eluent and recrystallizing the obtained product from hexane, the title compound is obtained in a yield of 1.66 g (67.6%), m.p.: 77°–92° C.

EXAMPLE 6

Preparation of
1-[(3α,16α)-eburnamenine-14-carbonyl]-4-(4
-chloro-2-pyrrolidino-6-pyrimidinyl)piperazine and
1-[(3α,16α)-eburnamenine-14-carbonyl]-4-(2-
chloro-4-pyrrolidino- 6-pyrimidinyl)piperazine After adding 2.00 g (3.81 mmoles) of 1-[(3α,16α)-eburnamenine- 14-carbonyl]-4-(2,4-dichloro-6-pyrimidinyl)piperazine in small portions to 20 ml of pyrrolidine at a temperature below 10° C., the reaction mixture is stirred at room temperature for 1 hour, then evaporated. After distributing the evaporation residue between 40 ml of chloroform and 10 ml of 1% sodium hydroxide solution the organic phase is separated, dried and evaporated. The evaporation residue is subjected to chromatography on a silica gel column. By using a 99:1 mixture of chloroform and methanol the less polar 1-[(3α,16α)-eburnamenine-14-carbonyl]-4-(4-chloro-2-pyrrolidino-6-pyrimidinyl)piperazine is first eluted from the column, which is recrystallized from a mixture of ether and hexane to give a yield of 2.01 g (88.2%), m.p.: 210°–220° C. By further elution the more polar 1-[(3α,16α)-eburnamenine-14-carbonyl]-4-(2-chloro-4-pyrrolidino-6-pyrimidinyl)piperazine is obtained which is similarly recrystallized from a mixture of ether and hexane to give a yield of 0.13 g (5.7%), m.p.: 169°–200° C.

EXAMPLE 7

Preparation of
1-[(3α,16α)-eburnamenine-14-carbonyl]-4-(4
-chloro-6-pyrrolidino-2-pyrimidinyl)piperazine 2.0 g (3.81 mmoles) of 1-[(3α,16α)-eburnamenine-14-carbonyl]-4-(4,6-dichloro-2-pyrimidinyl)piperazine are added in small portions to 20 ml of pyrrolidine at a temperature below 10° C., then the reaction mixture is stirred at room temperature for 1 hour and evaporated. The evaporation residue is distributed between 40 ml of chloroform and 10 ml of 10% sodium hydroxide solution. After separation the organic phase is dried and evaporated. The product obtained is recrystallized from a mixture of ether and hexane to give 2.10 g (92.2%) of the title compound, m.p.: 176°–181° C.

EXAMPLE 8

Preparation of
1-[(3α,16α)-eburnamenine-14-carbonyl]-4-(4
-chloro-2-pyrrolidino-6-pyrimidinyl)piperazine 5.0 g (12.8 mmoles) of 1-[(3α,16α)-eburnamenine-14-carbonyl]piperazine and 2.5 g (11.5 mmoles) of 4,6-dichloro-2 -pyrrolidinopyrimidine are dissolved in 100 ml of acetonitrile and, after adding 5.0 g of potassium carbonate, the reaction mixture is boiled under reflux for 40 hours, then evaporated. The evaporation residue is distributed between 100 ml of chloroform and 40 ml of water. After separation the organic phase is dried and evaporated. The product obtained is recrystallized from a mixture of ether and hexane to give 5.87 g (85.3%) of the title compound, m.p.: 210°–220° C.

EXAMPLE 9

Preparation of
1-[(3α,16α)-eburnamenine-14-carbonyl]-4-(4
-chloro-6-pyrrolidino-2-pyrimidinyl)piperazine and
1 -[(3α,16α)-eburnamenine-14-carbonyl]-4-
(2-chloro-4-pyrrolidino-6-pyrimidinyl)piperazine After dissolving 5.0 g (12.8 mmoles) of 1-[(3α,16α)-eburnamenine-14-carbonyl]piperazine and 2.5 g (11.5 mmoles) of 2,4-dichloro-6-pyrrolidinopyrimidine in 100 ml of acetonitrile and adding 5.0 g of potassium carbonate, the reaction mixture is boiled under reflux for 40 hours, then evaporated. The residue is distributed between 100 ml of chloroform and 40 ml of water. The organic phase is separated, dried and evaporated. The evaporation residue is subjected to chromatography on a silica gel column. By using a 99:1 mixture of chloroform and methanol as eluent, the less polar 1-[(3α,16α)-eburnamenine-14-carbonyl]-4-(4-chloro-6-pyrrolidino- 2-pyrimidinyl)piperazine is first eluted from the column, which is recrystallized from a mixture of ether and hexane to give a yield of 5.16 g (75.2%), m.p.: 176°–181° C. By further elution the more polar 1-[(3α,16α)-eburnamenine-14-carbonyl]-4-(2-chloro-4-pyrrolidino-6-pyrimidinyl)piperazine is eluted, which is similarly recrystallized from a mixture of ether and hexane to give a yield of 0.475 g (6.92%), m.p.: 169°–200° C.

EXAMPLE 10

Preparation of
1-[(3α,16α)-eburnamenine-14-carbonyl]-4-(4-
chloro-2-pyrrolidino-6-pyrimidinyl)piperazine To a solution containing 2.0 g (7.47 mmoles) of freshly prepared 4-chloro-6-(1-piperazinyl)-2-pyrrolidinopyrimidine in 20 m of methylene chloride, 2.96 g (7.84 mmoles) of (3α,16α)-eburnamenine-14-carbonyl chloride hydrochloride and 1.08 g of potassium carbonate are added in small portions at −15° C. Thereafter, the cooling of the reaction mixture is stopped, the mixture is allowed to warm to room temperature and then 10 ml of water are added. After stirring for 10 minutes and settling, the phases are separated, then the organic phase is washed with water twice, dried and evaporated. After recrystallizing the evaporation residue from a mixture of ether and hexane, the title compound is obtained in a yield of 4.03 g (90.3%), m.p.: 210°–220° C.

EXAMPLE 11

Preparation of
1-[(3α,16α)-eburnamenine-14-carbonyl]-4-(4
-chloro-6-pyrrolidino-2-pyrimidinyl)piperazine Freshly prepared 4-chloro-6-(1-piperazinyl)-2-pyrrolidinopyrimidine is reacted with (3α,16α)-eburnamenine-14-carbonyl chloride hydrochloride as described in Example 10 to obtain the title compound in a yield of 88.1%, m.p.: 176°–181° C.

EXAMPLE 12

Preparation of
4-chloro-2,6-bis(pyrrolidino)pyrimidine and
2-chloro-4,6-bis(pyrrolidino)pyrimidine 10 g of 2,4-dichloro-6-pyrrolidinopyrimidine are added in small portions to 40 ml of pyrrolidine at a temperature below 10° C. while stirring. After the addition the reaction mixture is stirred at room temperature for 1 hour, then evaporated. After distributing the residue between 150 ml of chloroform and 30 ml of 10% sodium hydroxide solution, the organic phase is separated, washed 4 times with 50 ml of water each, then dried and evaporated. The evaporation residue is subjected to chromatography on a silica gel column. By using a 19:1 mixture of hexane and ethyl acetate as eluent and recrystallizing the product from hexane, 11.07 g (83.74%) of 4-chloro-2,6-bis(pyrrolidino)pyrimidine are obtained, m.p.: 78°–81° C.

$^1$H-NMR (60 MHz, CDCl$_3$) δ ppm: 5.67 (s, 1H, 5-H)

By further elution with a 9:1 mixture the more polar 2-chloro-4,6-bis(pyrrolidino)pyrimidine is obtained, which is recrystallized from hexane to give a yield of 1.38 g (10.46%), m.p.: 92°–94° C.

$^1$H-NMR (60 MHz, CDCl$_3$) δ ppm: 4.91 (s, 1H, 5-H)

EXAMPLE 13

Preparation of
1-[(3α,16α)-eburnamenine-14-carbonyl]-4-(2,4
-bis(pyrrolidino)-6-pyrimidinyl)piperazine A solution of 1.00 g of 1-[(3α,16α)-eburnamenine-14-carbonyl]-4-(4-chloro-2-pyrrolidino-6-pyrimidinyl)piperazine in 10 ml of pyrrolidine is boiled under reflux for 5 hours, then evaporated. The evaporation residue is distributed between 20 ml of chloroform and 5 ml of 10% sodium hydroxide solution. After separation the organic phase is washed twice with water, then dried and evaporated. The evaporation residue is recrystallized from acetonitrile to give the title compound in a yield of 0.93 g (91.7%), m.p. 267°–269° C., $[α]_D^{21}$=−50.9° (c=2, 1M HCl).

EXAMPLE 14

Preparation of
1-[(3α,16α)-eburnamenine-14-carbonyl]-4-(2,6
-bis(pyrrolidino)-4-pyrimidinyl)piperazine By using 1-[(3α,16α)-eburnamenine-14-carbonyl]-4-(2-chloro-6-pyrrolidino-4-pyrimidinyl)piperazine as starting material, the process described in Example 13 is followed to obtain the title compound in a yield of 89.6%, m.p.: 267°–269° C.

EXAMPLE 15

Preparation of
1-[(3α,16α)-eburnamenine-14-carbonyl]-4-(2,6
-bis(pyrrolidino)-4-pyrimidinyl)piperazine A solution containing 2.0 g (5.12 mmoles) of 1-[(3α,16α)-eburnamenine-14-carbonyl]piperazine and 3.88 g (15.36 mmoles) of 4-chloro-2,6-bis(pyrrolidino)pyrimidine in 30 ml of N-ethylmorpholine is refluxed under nitrogen for 40 hours, then the reaction mixture is evaporated under environmental pressure. Thereafter, 30 ml of water are added and water is distilled off until the temperature of the vapor reaches 100° C. After cooling down the residue is distributed between 50 ml of chloroform and 10 ml of 10% sodium hydroxide solution. After separation the organic phase is dried and evaporated. The evaporation residue is purified by chromatography on a silica gel column. By using a mixture of chloroform and methanol (99:1→95:5) as eluent and recrystallizing the obtained product from ethanol, the title compound is obtained in a yield of 2.84 g (91.3%), m.p.: 267°–269° C.

EXAMPLE 16

Preparation of
1-[(3α,16α)-eburnamenine-14-carbonyl]-4-[2,6
-bis(pyrrolidino)-4-pyrimidinyl]piperazine 1-[(3α,16α)-eburnamenine-14-carbonyl]-4-(2,4-dichloro-6-pyrimidinyl)piperazine is reacted with pyrrolidine as described in Example 13 to give the title compound in a yield of 89.3%, m.p.: 267°–269° C.

EXAMPLE 17

Preparation of
2-(1-piperazinyl)-4,6-bis(pyrrolidino)pyrimidine

A mixture of 10.0 g (34.7 mmoles) of 2-chloro-2,6-bis(pyrrolidino)pyrimidine, 11.95 g (138.8 mmoles) of piperazine and 150 ml of N-ethylmorpholine is boiled under reflux under nitrogen for 25 hours, then the solvent and excess piperazine are distilled off under environmental pressure. After adding 100 ml of water to the residue, water is distilled off until the head temperature reaches 100° C. After cooling down, the residue is distributed between 200 ml of chloroform and 30 ml of 10% sodium hydroxide solution. After separation the organic phase is washed 4 times with 50 ml of water each, then dried and evaporated. The evaporation residue is purified by chromatography on a silica gel column. By using a 9:1 mixture of chloroform and methanol as eluent and recrystallizing the product from hexane, the title compound is obtained in a yield of 8.54 g (81.4%), m.p.: 152°–160° C.

$^1$H-NMR (60 MHz, CDCl$_3$) δ ppm: 4.83 (s, 1H, 5-H)

EXAMPLE 18

Preparation of
1-[(3α,16α)-eburnamenine-14-carbonyl]-4
-[4,6-bis(pyrrolidino)-2-pyrimidinyl]piperazine 1-[(3α,16α)-eburnamenine-14-carbonyl]-4-(4-chloro-6-pyrrolidino-2-pyrimidinyl)piperazine is reacted with pyrrolidine as described in Example 13 to give the title compound in a yield of 90.2%, m.p.: 275°–278° C.

EXAMPLE 19

Preparation of
1-[(3α,16α)-eburnamenine-14-carbonyl]-4-
[4,6-bis(pyrrolindino)-2-pyrimidinyl]piperazine 1-[(3α,16α)-eburnamenine-14-carbonyl]piperazine is reacted with 2-chloro-4,6-bis(pyrrolidino)pyrimidine as described in Example 15 to obtain the title compound in a yield of 89.5%, m.p.: 274°–277° C.

EXAMPLE 20

Preparation of
1-[(3α,16α)-eburnamenine-14-carbonyl]-4-[4,6-bis(pyrrolidino)-2-pyrimidinyl]piperazine First 1.31 g (3.47 mmoles) of (3α,16α)-eburnamenine-14-carbonyl chloride hydrochloride and then 0.48 g of potassium carbonate are added in small portions to a solution of 1.0 g (3.31 mmoles) of 2-(1-piperazinyl)-4,6-bis(pyrrolidino)pyrimidine in 10 ml of methylene chloride at −15° C. Then the cooling of the reaction mixture is stopped, the temperature of the mixture is allowed to reach room temperature and 5 ml of water are added. After stirring for 10 minutes and settling, the phases are separated, the organic phase is washed twice with water, then dried and evaporated. The evaporation residue is recrystallized from acetonitrile. The product obtained is dried and recrystallized from ethanol to give the title compound in a yield of 1.81 g (90.3%), m.p.: 275°–278° C.

EXAMPLE 21

Preparation of
1-[(3α,16α-eburnamenine-14-carbonyl]-4-[4,6-bis(pyrrolidino)-2-pyrimidinyl]piperazine 1-[(3α,16α)-eburnamenine-14-carbonyl]-4-(4,6-dichloro-2-pyrimidinyl)piperazine is brought into reaction with pyrrolidine as described in Example 13 to give the title compound in a yield of 89%, m.p.: 275°–278° C.

EXAMPLE 22

Preparation of
1-[(16α)-eburnamenine-14-carbonyl]-4-[2,6-bis(pyrrolidino-)-pyrimidinyl]piperazine (16α)-Eburnamenine-14-carbonyl chloride hydrochloride is reacted with piperazine as described in Example 1, then the product obtained is brought into reaction with 4-chloro-2,6-bis(pyrrolidino)pyrimidine as described in Example 15 to obtain the title compound in a yield of 87.7%, m.p.: 235°–238° C., $[\alpha]_D^{25}=+20°$ (c=1, 1M HCl).

EXAMPLE 23

Preparation of
1-[(3α)-eburnamenine-14-carbonyl]-4-[2,6-bis(pyrrolidino)-4-pyrimidinyl]piperazine (3α)-Eburnamenine-14-carbonyl chloride hydrochloride is reacted with piperazine as described in Example 1 and the product obtained is brought into reaction with 4-chloro-2,6-bis(pyrrolidino)pyrimidine according to Example 15 to give the title compound in a yield of 89.4%, m.p.: 241°–243° C., $[\alpha]_D^{25}=+19°$ (c=1, 1M HCl).

EXAMPLE 24

Preparation of
4,6-dichloro-2-(1-adamantylamino)pyrimidine and
2,6-dichloro-4-(1-adamantylamino)pyrimidine To a solution of 70.3 g (465.6 mmoles) of 1-aminoadamantane in 650 ml of tetrahydrofuran 40.6 g (225.6 mmoles) of 2,4,6-trichloropyrimidine are added, and the reaction mixture is stirred for 24 hours. Thereafter, the crystalline 1-aminoadamantane hydrochloride is filtered off, the filtrate is evaporated and the residue is subjected to chromatography on a silica gel column. By using a 49:1 mixture of hexane and acetone as eluent 4,6-dichloro-2-(1-adamantylamino)pyrimidine is obtained which is recrystallized from hexane to give a yield of 28.74 (43.5%), m.p.: 151°–155° C.

$^1$H-NMR (60 MHz, CDCl$_3$) δ ppm: 6.55 (s, 1H, 5-H)

By further elution with a 24:1 mixture of hexane and acetone the more polar 2,6-dichloro-4-(1-adamantylamino)pyrimidine is obtained, which is recrystallized from hexane to obtain a yield of 35.56 g (53.8%), m.p. 193°–196° C.

$^1$H-NMR (60 MHz, CDCl$_3$) δ ppm: 6.33 (s, 1H, 5-H)

EXAMPLE 25

Preparation of
2,4-bis(1-adamantylamino)-6-chloropyrimidine

A solution containing 26.0 g (87.25 mmoles) of 4,6-dichloro-2-(1-adamantylamino)pyrimidine and 39.5 g (261.6 mmoles) of 1-aminoadamantane in 200 ml of n-butanol is boiled under reflux for 75 hours, then evaporated. The evaporation residue is suspended in 400 ml of ether, the suspension is filtered off and, after drying, the product filtered off is purified by chromatography on a silica gel column. By using chloroform as eluent and recrystallizing the obtained product from ether the title compound is obtained in a yield of 23.94 g (66.44%), m.p.: 232°–236° C.

$^1$H-NMR (60 MHz, CDCl$_3$) δ ppm: 5.64 (s, 1H, 5-H)

EXAMPLE 26

Preparation of
2,4-bis(1-adamantylamino)-6-(1-piperazinyl)pyrimidine 2,4-bis(1-adamantylamino)-6-chloropyrimidine is reacted with piperazine as described in Example 17 to give the title compound in a yield of 83.36%, m.p. 168°–175° C.

$^1$H-NMR (60 MHz, CDCl$_3$) δ ppm: 4.97 (s, 1H, 5-H)

EXAMPLE 27

Preparation of
1-[(3α,16α)-eburnamenine-14-carbonyl]-4-[2,4-bis(1-adamantylamino)-6-pyrimidinyl]-piperazine (3α,16α)-Eburnamenine-14-carbonyl chloride hydrochloride is reacted with 2,4-bis(1-adamantylamino)-6-(1-piperazinyl)pyrimidine as described in Example 20 to obtain the title compound in a yield of 84.6%, m.p. 270°–273° C.

EXAMPLE 28

Preparation of
2-(1-adamantylamino)-4-chloro-6-pyrrolidinopyrimidine 10 g (33.53 mmoles) of 4,6-dichloro-2-(1-adamantylamino)pyrimidine are added in small portions to 40 ml of pyrrolidine at a temperature below 10° C. under cooling and stirring. After addition the reaction mixture is stirred at room temperature for 1 hour, then evaporated. The residue is distributed between 150 ml of chloroform and 30 ml of 10% sodium hydroxide solution. After separation the organic phase is washed 4 times with 50 ml of water each, then dried and evaporated. The evaporation residue is recrystallized from ethyl acetate to give the title compound in a yield of 9.60 g (86%), m.p.: 178°–180° C.

$^1$H-NMR (60 MHz, CDCl$_3$) δ ppm: 5.62 (s, 1H, 5-H)

EXAMPLE 29

Preparation of
2-(1-adamantylamino)-4-(1-piperazinyl)-6-pyrrolidinopyrimidine 2-(1-Adamantylamino)-4-chloro-6-pyrrolidinopyrimidine is reacted with piperazine as described in Example 17 to give the title compound in a yield of 69.7%, m.p.: 160°–164° C.

$^1$H-NMR (60 MHz, CDCl$_3$) δ ppm: 4.87 (s, 1H, 5-H)

EXAMPLE 30

Preparation of
1-[(3α,16α)-eburnamenine-14-carbonyl]-4-[2-(1-adamantylamino)-6-pyrrolidino-4-pyrimidinyl]piperazine (3α,16α)-Eburnamenine-14-carbonyl chloride hydrochloride is reacted with 2-(1-adamantylamino)-4-(1-piperazinyl)-6-pyrrolidinopyrimidine as described in Example 20 to obtain the title compound in a yield of 88.8%, m.p.: 242°–246° C.

EXAMPLE 31

Preparation of
4,6-dichloro-2-(1,1-dimethylethylamino)pyrimidine
and
2,6-dichloro-4-(1,1-dimethylethylamino)pyrimidine 25 g (136.3 mmoles) of 2,4,6-trichloropyrimidine are dropwise added to a mixture of 31.52 ml (300 mmoles) of 1-amino-1,1-dimethylethane and 200 ml of tetrahydrofuran at a temperature between 10° C. and 15° C. under cooling and stirring. Subsequently, the reaction mixture is stirred at room temperature for an additional 5 hours, then evaporated. After distributing the residue between 500 ml of chloroform and 50 ml of 10% sodium hydroxide solution and separation, the organic phase is washed 4 times with 150 ml of water each, then dried and evaporated. The evaporation residue is subjected to chromatography on a silica gel column. By using a 9:1 mixture of hexane and ethyl acetate as eluent 4,6-dichloro- 2-(1,1-dimethylethylamino)pyrimidine is obtained, which is recrystallized from hexane to give a yield of 11.35 g (37.84%), m.p.: 70°–74° C.

$^1$H-NMR (60 MHz, THF-d$_8$) δ ppm: 6.63 (s, 1H, 5-H)

By further elution with a 4:1 mixture of hexane and ethyl acetate the more polar 2,6-dichloro-4-(1,1-dimethylethylamino)pyrimidine is obtained, which is recrystallized from ethyl acetate to obtain a yield of 13.31 g (44.35%), m.p.: 192°–195° C.

$^1$H-NMR (60 MHz, THF-d$_8$) δ ppm: 6.32 (s, 1H, 5-H)

EXAMPLE 32

Preparation of
4-chloro-2-(1,1-dimethylethylamino)-6-pyrrolidinopyrimidine 4,6-Dichloro-2-(1,1-dimethylethylamino)pyrimidine is reacted with pyrrolidine as described in Example 28 to give the title compound in a yield of 93%, m p.: 153°–157° C.

$^1$H-NMR (60 MHz, CDCl$_3$) δ ppm: 5.67 (s, 1H, 5-H)

EXAMPLE 33

Preparation of
2-(1,1-dimethylethylamino)-4-(1-piperazinyl)-6-pyrrolidinopyrimidine 4-Chloro-2-(1,1-dimethylethylamino)-6-pyrrolidinopyrimidine is reacted with piperazine as described in Example 17 to obtain the title compound in a yield of 78.1%, m.p.: 162°–165° C.

$^1$H-NMR (60 MHz, CDCl$_3$) δ ppm: 4.87 (s, 1H, 5-H)

EXAMPLE 34

Preparation of
1-[(3α,16α)-eburnamenine-14-carbonyl]-4-[2-(1,1-dimethylethylamino)-6-pyrrolidino-4-pyrimidinyl]piperazine (3α,16α)-Eburnamenine-14-carbonyl chloride hydrochloride is reacted with 2-(1,1-dimethylethylamino)-4-(1-piperazinyl)-6-pyrrolidinopyrimidine as described in Example 20 to give the title compound in a yield of 94.7%, m.p.: 225°–228° C.

EXAMPLE 35

Preparation of
4,6-dichloro-2-(2,2-dimethylpropylamino)pyrimidine
and
2,6-dichloro-4-(2,2-dimethylpropylamino)pyrimidine 25 g (136.3 mmoles) of 2,4,6-trichloropyrimidine are dropwise added to a mixture of 23.84 g (273.5 mmoles) of 1-amino-2,2-dimethylpropane and 200 ml of tetrahydrofuran at a temperature between 10° C. and 15° C. while stirring and cooling. Thereafter, the reaction mixture is stirred at room temperature for an additional 30 minutes, then evaporated. After distributing the evaporation residue between 300 ml of chloroform and 50 ml of 10% sodium hydroxide solution, the organic phase is separated, washed 4 times with 100 ml of water each, then dried and evaporated. The evaporation residue is subjected to chromatography on a silica gel column. By using a 19:1 mixture of hexane and ethyl acetate, 4,6-dichloro- 2-(2,2-dimethylpropylamino)pyrimidine is obtained, which is recrystallized from a mixture of ether and hexane to obtain a yield of 13.60 g (42.6%), m.p.: 63°–66° C.

$^1$H-NMR (60 MHz, CDCl$_3$) δ ppm: 6.60 (s, 1H, 5-H)

By further elution with a 6:1 mixture of hexane and ethyl acetate, the more polar 2,6-dichloro-4-(2,2-dimethylpropylamino)pyrimidine is obtained which is recrystallized from a mixture of ether and hexane to give a yield of 14.24 g (44.6%), m.p.: 77°–79° C.

$^1$H-NMR (60 MHz, CDCl$_3$) δ ppm: 6.33 (s, 1H, 5-H)

EXAMPLE 36

Preparation of
4-chloro-2-(2,2-dimethylpropylamino)-6-pyrrolidinopyrimidine

The reaction of 4,6-dichloro-2-(2,2-dimethylpropylamino)pyrimidine with pyrrolidine as described in Example 28 gives the title compound in a yield of 96.7%, m p.: 147°–150° C.

$^1$H-NMR (60 MHz, CDCl$_3$) δ ppm: 5.67 (s, 1H, 5-H)

EXAMPLE 37

Preparation of
2-(2,2-dimethylpropylamino)-4-(1-piperazinyl)-6-pyrrolidinopyrimidine The reaction of 2-(2,2-dimethylpropylamino)-4-chloro-6-pyrrolidinopyrimidine with piperazine as described in Example 17 leads to the title compound in a yield of 76%, m.p.: 118°–120° C.

$^1$H-NMR (60 MHz, CDCl$_3$) δ ppm: 4.83 (s, 1H, 5-H)

EXAMPLE 38

Preparation of
1-[(3α,16α)-eburnamenine-14-carbonyl]-4-[2-(2,2-dimethylpropylamino)-6-pyrrolidino-4-pyrimidinyl]piperazine (3α,16α)-Eburnamenine-14-carbonyl chloride hydrochloride is brought into reaction with 2-(2,2-dimethylpropylamino)-4-(1-piperazinyl)-6-pyrrolidinopyrimidine as described in Example 20 to give the title compound in a yield of 81.0%, m.p.: 266°–272° C.

EXAMPLE 39

Preparation of
1-[(3α,16α)-eburnamenine-14-carbonyl]-4-[2-(4-morpholinyl)-4-ethylamino-6-pyrimidinyl]piperazine The reaction of 2-(4-morpholinyl)-4-ethylamino-6-(1-piperazinyl)pyrimidine (which is known from the GB patent specification No. 1,345,640) with (3α,16α)-eburnamenine-14-carbonyl chloride hydrochloride as described in Example 20 gives the title compound.

EXAMPLE 40

Preparation of
1-[(3α,16α)-eburnamenine-14-carbonyl]-4-[2-amino-4-(1,1-dimethylethylamino)-6-pyrimidinyl]piperazine The reaction of 1-[(3α,16α)-eburnamenine-14-carbonyl]piperazine with 2-amino-4-chloro-6-(1,1-dimethylethylamino)pyrimidine (known from the German patent specification No. 2,006,145) as described in Example 15 results in the title compound.

EXAMPLE 41

Preparation of
2-cyclopentylamino-4,6-dichloropyrimidine and 4-cyclopentylamino-2,6-dichloropyrimidine The reaction of 2,4,6-trichloropyrimidine with cyclopentylamine carried out as described in Example 35 gives both compounds. The less polar 2-cyclopentylamino-4,6-dichloropyrimidine is obtained in a yield of 35.2%, m.p.: 48°–52° C.

$^1$H-NMR (60 MHz, CDCl$_3$) δ ppm: 6.52 (s, 1H, 5-H)

The more polar 4-cyclopentylamino-2,6-dichloropyrimidine is obtained in an oily form in a yield of 57.2%.

$^1$H-NMR (60 MHz, CDCl$_3$) δ ppm: 6.30 (s, 1H, 5-H)

EXAMPLE 42

Preparation of
2-cyclopentylamino-4-chloro-6-pyrrolidinopyrimidine

The reaction of 2-cyclopentylamino-4,6-dichloropyrimidine with pyrrolidine as described in Example 13 gives the title compound as an oily product in a yield of 72.4%.

$^1$H-NMR (60 MHz, CDCl$_3$) δ ppm: 5.72 (s, 1H, 5-H)

EXAMPLE 43

Preparation of
1-[(3α,16α)-eburnamenine-14-carbonyl]-4-(2-cyclopentylamino-6-pyrrolidino-4-pyrimidinyl)piperazine The title compound is prepared by reacting 1-[(3α,16α)-eburnamenine- 14-carbonyl]piperazine with 2-cyclopentylamino- 4-chloro-6-pyrrolidinopyrimidine as described in Example 15.

EXAMPLE 44

Preparation of
4,6-dichloro-2-(2,2,6,6-tetramethyl-1-piperidinyl)pyrimidine

A mixture containing 25 g (136.3 mmoles) of 2,4,6-trichloropyrimidine and 46.3 ml (272.6 mmoles) of 2,2,4,4-tetramethylpiperidine is boiled under reflux for 50 hours, then cooled down and suspended in 250 ml of hexane. The insoluble part is filtered off, the filtrate is evaporated and the evaporation residue is distributed between 300 ml of chloroform and 50 ml of 10% sodium hydroxide solution. After separation the organic phase is washed 4 times with 100 ml of water each, then dried and evaporated. The evaporation residue is purified by chromatography on a silica gel column. By using hexane as eluent the title compound is obtained, which is recrystallized to give a yield of 8.04 g (20.47%), m.p.: 89°–90° C.

$^1$H-NMR (60 MHz, CDCl$_3$) δ ppm: 6.53 (s, 1H, 5-H)

EXAMPLE 45

Preparation of
4-chloro-2-(2,2,6,6-tetramethyl-1-piperidinyl)-6-pyrrolidinopyrimidine The reaction of 4,6-dichloro-2-(2,2,6,6-tetramethyl-1-piperidinyl)pyrimidine with pyrrolidine as described in Example 13 gives the title compound in a yield of 75.08%, m.p.: 130°–135° C.

$^1$H-NMR (60 MHz, CDCl$_3$) δ ppm: 5.76 (s, 1H, 5-H)

EXAMPLE 46

Preparation of
1-[(3α,16α)-eburnamenine-14-carbonyl]-4-[2-(2,2,6,6-tetramethyl-1-piperidinyl)-6-pyrrolidino-4-pyrimidinyl]piperazine The title compound is prepared by reacting 1-[(3α,16α)-eburnamenine- 14-carbonyl]piperazine with 4-chloro-2-(2,2,6,6-tetramethyl-1-piperidinyl)-6-pyrrolidinopyrimidine similarly as described in Example 15.

EXAMPLE 47

Preparation of
1-[(3α,16α)-eburnamenine-14-carbonyl]-
(hexahydro-1H-1,4-diazepine)

The reaction of (3α,16α)-eburnamenine-14-carbonyl chloride hydrochloride with homopiperazine similarly as described in Example 1 gives the title compound.

EXAMPLE 48

Preparation of
1-[(3α,16α)-eburnamenine-14-carbonyl]-4-[2,6
-bis(pyrrolidino)-4-pyrimidinyl]-
(hexahydro-1H-1,4-diazepine)

The title compound is prepared by reacting 1-[(3α,16α)-eburnamenine- 14-carbonyl]-(hexahydro-1H-1,4-diazepine) with 4-chloro-2,6-bis(pyrrolidino)pyrimidine similarly as described in Example 15.

EXAMPLE 49

Preparation of
1-[(3α,16α)-eburnamenine-14-ylmethyl]-4-[2,6
-bis(pyrrolidino)-4-pyrimidinyl]piperazine A solution containing 1.95 g (3.2 mmoles) of 1 -[(3α, 16α)-eburnamenine-14-carbonyl]-4-[2,6-bis(pyrrolidino)-4-pyrimidinyl]piperazine in 65 ml of tetrahydrofuran is dropwise added over 10 minutes to 1.3 g (34 mmoles) of lithium aluminum hydride dissolved in 65 ml of tetrahydrofuran under argon while stirring, then the reaction mixture is boiled under reflux for 3 hours. After cooling down, the excess of the reducing agent is decomposed by successively adding a mixture of 1.3 ml of water and 1.3 ml of 15% sodium hydroxide solution and then 5.2 ml of water. After filtering off the precipitate and washing it with tetrahydrofuran, the filtrate combined with the washings is evaporated. The evaporation residue is purified on a silica gel column. By using a 9:1 mixture of cyclohexane and diethylamine as eluent, the title compound is obtained as a foam in a yield of 1.00 g, $[α]_D^{22}=-33°$ (as trihydrobromide, c=1, $H_2O$).

EXAMPLE 50

Preparation of
1-[(3α,16α)-eburnamenine-14-ylmethyl]-4-[2,6-bis
(pyrrolidino)- 4-pyrimidinyl]piperazine
trihydrobromide After suspending 1.00 g (1.69 mmoles) of 1-[(3α,16α)-eburnamenine- 14-ylmethyl]-4-[2,6-bis(pyrrolidino)-4-pyrimidinyl]piperazine in 10 ml of isopropanol, 2.02 ml (5.06 mmoles) of a 2.5M solution of hydrogen bromide in isopropanol are added to the above suspension. The crystalline precipitate is filtered off and dried to obtain 0.65 g (46%) of the title salt.

EXAMPLE 51

Preparation of an injectable solution 0.05% by weight of sodium pyrosulfite is dissolved in oxygen-free water for injection and the active ingredient is dissolved therein. Simultaneously, 0.1% by weight of potassium sorbate is dissolved in oxygen-free water for injection and sodium chloride in an amount required for isotonization is dissolved therein. After combining both solutions, the solution is filled up to the final volume desired with oxygen-fee water for injection and finally, it is filtered through a membrane filter with 0.2 μm pore diameter for making it free of bacteria and strange materials. The filtrate is filled into ampoules under nitrogen.

A preferable composition of 1 ml volume of injection is as follows:

| active ingredient | 10 mg |
| sodium pyrosulfite | 5 mg |
| sodium chloride | 7 mg |
| water for injection | up to 1 ml |

We claim:
1. A compound of the formula

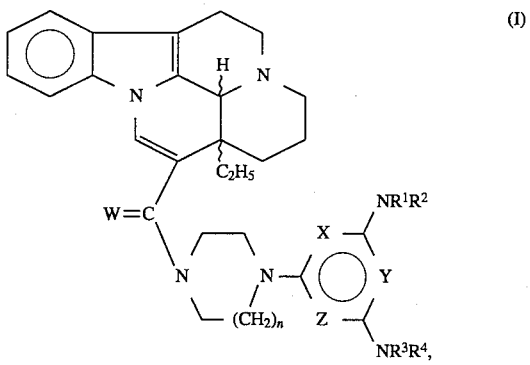

(I)

wherein
$R^1$ and $R^2$ as well as $R^3$ and $R^4$, independently from each other, are hydrogen, $C_{2-6}$alkyl group, $C_{2-6}$alkenyl group; or a $C_{3-10}$alicyclic group involving 1 to 3 rings, and this latter group may be substituted by a $C_{1-6}$alkyl or $C_{2-6}$alkenyl group; or $R^1$ and $R^2$ and/or $R^3$ and $R^4$, together with the adjacent nitrogen atom and optionally with an additional oxygen or nitrogen atom, form a 4- to 6-membered, saturated or unsaturated cyclic group which may be substituted by a $C_{1-6}$alkyl or $C_{2-6}$alkenyl group;

two of x, Y and Z are nitrogen whereas the third of them is a methine group;

n is 1 or 2;

W is oxygen or two hydrogen atoms; and the wavy line means α-/α-, α-/β- or β-/α- steric position, or a pharmaceutically acceptable acid addition salt or solvate thereof.

2. A method for inhibiting peroxidation of lipids in a mammalian subject which comprises the step of administering to said mammal a therapeutically effective amount of the compound of the formula (I), as defined in claim 1, or a pharmaceutically acceptable acid addition salt or solvate thereof.

3. A pharmaceutical composition for inhibiting lipid peroxidation, which comprises as active ingredient a therapeutically effective amount of the compound of the formula (I), as defined in claim 1, or a pharmaceutically acceptable acid addition salt or solvate thereof.

4. A compound selected from the group consisting of
1-[(3α,16α)-eburnamenine-14-carbonyl]-4-[2,4 -bis(pyrrolidino)-6-pyrimidinyl]piperazine,
1-[(3α,16α)-eburnamenine-14-carbonyl]-4-[2,6 -bis(pyrrolidino)-4-pyrimidinyl]piperazine,
1-[(3α,16α)-eburnamenine-14-carbonyl]-4-[4,6 -bis(pyrrolidino)-2-pyrimidinyl]piperazine, 1-[(16α)-eburnamenine-14-carbonyl]-4-[2,6-bis(pyrrolidino)-4-pyrimidinyl]piperazine, 1-[(3α)-eburnamenine-14-carbonyl]-4-[2,6-bis(pyrrolidino)-4-pyrimidinyl]piperazine, 1-[(3α,16α)-eburnamenine-14-carbonyl]-4-[2,4-bis(1-adamantylamino)-6-pyrimidinyl]piperazine, 1-[(3α,16α)-eburnamenine-14-carbonyl]-4-[2-(1-adamantylamino)-6-pyrrolidino-4-pyrimidinyl]piperazine, 1-[(3α,16α)-eburnamenine-14-carbonyl]-4-[2-(1,1-dimethylethylamino)-6-pyrrolidino-4-pyrimidinyl]piperazine, 1-[(3α,16α)-eburnamenine-14-carbonyl]-4-[2-(2,2-dimethylpropylamino)-6-pyrrolidino-4-pyrimidinyl]piperazine, 1-[(3α,16α)-eburnamenine-14-carbonyl]-4-[2-(4-morpholinyl)-4-ethylamino-6-pyrimidinyl]piperazine, 1-[(3α,16α)-eburnamenine-14-carbonyl]-4-[2-amino-4-(1,1-dimethylethylamino)-6-pyrimidinyl]piperazine, 1-[(3α,16α)-eburnamenine-14-carbonyl]-4-(2-cyclopentylamino-6-pyrrolidino-4-pyrimidinyl)piperazine, 1-[(3α,16α)-eburnamenine-14-carbonyl]-4-[2-(2,2,6,6-tetramethyl-1-piperidinyl)-6-pyrrolidino-4-pyrimidinyl]piperazine, 1-[(3α,16α)-eburnamenine-14-carbonyl]-4-[2,6-bis(pyrrolidino)-4-pyrimidinyl]-hexahydro-1H-1,4-diazepine, and 1-[(3α,16α)-eburnamenine-14-carbonyl]-4-[2,6-bis(pyrrolidino)-4-pyrimidinyl]piperazine or pharmaceutically acceptable acid addition salts of these compounds.

* * * * *